(12) United States Patent
Xu (10) Patent No.: US 9,585,595 B2
(45) Date of Patent: Mar. 7, 2017

(54) MULTIPLE CHANNEL NUCLEAR MAGNETIC RESONANCE COIL

(71) Applicant: Shenzhen RF Tech Co., Ltd., Shenzhen (CN)

(72) Inventor: Jixin Xu, Shenzhen (CN)

(73) Assignee: SHENZHEN RF TECH CO., LTD., Shenzhen (CN)

( * ) Notice: Subject to any disclaimer, the term of this patent is extended or adjusted under 35 U.S.C. 154(b) by 505 days.

(21) Appl. No.: 14/259,243

(22) Filed: Apr. 23, 2014

(65) Prior Publication Data

US 2014/0333305 A1 Nov. 13, 2014

(30) Foreign Application Priority Data

May 8, 2013 (CN) .......................... 2013 1 0166491

(51) Int. Cl.
*G01R 33/3415* (2006.01)
*G01R 33/36* (2006.01)
*A61B 5/055* (2006.01)

(52) U.S. Cl.
CPC .......... *A61B 5/055* (2013.01); *G01R 33/3415* (2013.01); *G01R 33/365* (2013.01)

(58) Field of Classification Search
CPC .... G01R 33/3415; G01R 33/365; A61B 5/055
See application file for complete search history.

(56) References Cited

U.S. PATENT DOCUMENTS

| | | | | |
|---|---|---|---|---|
| 5,057,778 A | * | 10/1991 | Rath ................... | G01R 33/3635 324/318 |
| 8,866,481 B2 | * | 10/2014 | Zhu .................... | G01R 33/3415 324/318 |
| 9,116,214 B2 | * | 8/2015 | Yang ................... | G01R 33/3664 |
| 2008/0297154 A1 | * | 12/2008 | Otake ............... | G01R 33/34046 324/318 |
| 2013/0093425 A1 | * | 4/2013 | Chu ..................... | G01R 33/365 324/318 |

* cited by examiner

*Primary Examiner* — Rodney Bonnette
(74) *Attorney, Agent, or Firm* — Pillsbury Winthrop Shaw Pittman LLP (57) ABSTRACT

A multi-channel nuclear magnetic resonance (NMR) coil operating at a resonance frequency includes a plurality of unit loops disposed upon a cylindrical surface of a coil body and surrounding the coil body as a closed NMR coil; and a plurality of inter-loop capacitors configured to connect adjacent unit loops respectively, wherein each unit loop comprises a signal channel and further comprises a pair of vertical conducting parts parallel to a cylindrical axis of the coil body, each vertical conducting part comprising an inductor and a first capacitor connected in serial; and a pair of horizontal conducting parts perpendicular to the cylindrical axis of the coil body, at least one horizontal conducting part comprising a second capacitor; and the inter-loop capacitor connects two respective horizontal conducting parts of adjacent unit loops disposed on a same side to eliminate coupling between signal channels of adjacent unit loops.

18 Claims, 7 Drawing Sheets

MULTIPLE CHANNEL NUCLEAR MAGNETIC RESONANCE COIL

RELATED APPLICATIONS

This application claims priority to Chinese Patent Application No. 201310166491.2, "A MULTIPLE CHANNEL NUCLEAR MAGNETIC RESONANCE COIL," filed on May 8, 2013, which is hereby incorporated by reference in its entirety.

FIELD OF THE INVENTION

The present invention relates to a nuclear magnetic resonance (NMR) imaging system, and specifically relates to a multiple channel NMR coil.

BACKGROUND OF THE INVENTION

An NMR imaging system is a device that generates 2-D or 3-D sample images based on the principles of NMR imaging, and is more and more widely used in the medical diagnosis field. An NMR system normally comprises a magnet for generating a static uniform magnetic field $B_0$ that is large enough to cover the imaged region of the patient body; a radio frequency (RF) system comprising an RF transmit coil for exciting the resonance of the sample and an RF receive coil for receiving resonance signals from the sample; a gradient system for generating a gradient magnetic field in the sample space and ensuring convenient image coding; and a computer imaging system for receiving the signals collected by the RF receive coil and generating visual images that can be conveniently observed by the doctor.

In the NMR imaging technique, the receive coil collects the RF signals from the excited sample, and the collected RF signals are then magnified for sample image reconstruction. The electrical structure of the receive coil comprises a coil body made of conducting materials; and inductors and capacitors that are connected into the coil body. When the receive coil works, it surrounds the examined region of the patient and its output impedance matches a back-end data collecting device. Moreover, uniform electromagnetic field distribution is achieved inside the coil at the operating frequency, and output resonance signal has an excellent signal to noise ratio (SNR) so as to gain a sharp and undistorted sample image. When the receive coil idles, it is detuned and does not affect the function of the transmit coil and other devices in the system.

In current techniques, a multiple channel NMR receive coil is usually constructed comprising two or more closed unit loops that surround the periphery of the imaged region. By increasing the number of the unit loops, a stronger electromagnetic signal theoretically may be obtained in less time, but more complicated tuning is necessary to gain an excellent SNR and a sharp sample image. The reason is that as the channels increase, the coupling of unit loops becomes more complicated. The coupling of adjacent unit loops can be eliminated by an overlap or by a direct series connection of inductors and capacitors. However, the coupling of nonadjacent unit loops is difficult to eliminate. If the coupling of unit loops cannot be eliminated, a multiple channel coil will not properly function.

SUMMARY

A main object of the present invention is to provide an NMR receive coil comprising multiple channel unit loops, by which a stronger NMR signal and an excellent SNR may be obtained in less time.

The present invention discloses a multiple channel nuclear magnetic resonance (NMR) coil, operating at a resonance frequency $f_0$ comprising five or more closed signal channels, each comprising a unit loop, the unit loops being arranged on and surrounding a cylindrical surface of a periphery of an imaged region, and each unit loop comprises two vertical conducting parts parallel to a cylinder axis; and two arc-shaped conducting parts perpendicular to the cylinder axis; wherein the vertical conducting part of the unit loop comprise an inductor and a capacitor connected in serial, forming a resonant circuit with another inductor and capacitor in an adjacent unit loop or a nonadjacent unit loop separated by one unit loop to decrease coupling between signal channels of adjacent unit loops or nonadjacent unit loops separated by one unit loop; and a plurality of inter-loop capacitors configured to respectively connect the two arc-shaped conducting parts disposed on one same side of adjacent unit loops to decrease coupling between multiple signal channels.

In accordance with some embodiments, at least one arc-shaped conducting part of each unit loop further comprises an intra-loop capacitor to decrease the coupling between multiple signal channels.

In accordance with some embodiments, both arc-shaped conducting parts of each unit loop comprise an intra-loop capacitor, respectively, and the plurality of inter-loop capacitors are further configured to respectively connect the arc-shaped conducting parts disposed on both same sides of adjacent unit loops.

In accordance with some embodiments, each unit loop overlaps with an adjacent unit loop to form an overlapped area that generates a mutual inductance, forming the resonant circuit by coupling the mutual inductance with two respective capacitors of adjacent unit loops to decrease the coupling of adjacent signal channels.

In accordance with some embodiments, two respective inductors of adjacent unit loops or nonadjacent unit loops separated by one unit loop generate an eddy current that offsets a coupling eddy current to decrease the coupling between adjacent signal channels or nonadjacent signal channels separated by one signal channel.

In accordance with some embodiments, the unit loops are further configured to change a size of the overlapped area to decrease the coupling of adjacent signal channels.

In accordance with some embodiments, a size of the overlap area is configured such that the coupling of adjacent unit loops is less than −15 dB.

In accordance with some embodiments, the multiple channel nuclear magnetic resonance (NMR) coil further comprises eight unit loops arranged on and surrounding the cylindrical surface, wherein the inter-loop capacitor is configured with a capacitance of 10 pF.

In accordance with some embodiments, the unit loop further comprises a detuning circuit configured to detune the unit loop in a preset time period.

In accordance with some embodiments, a vertical height of the overlapped area is configured to be 3 mm.

In yet another embodiment, a multi-channel nuclear magnetic resonance (NMR) coil operating at a resonance frequency comprises a plurality of unit loops disposed upon a cylindrical surface of a coil body and surrounding the coil body as a closed NMR coil; and a plurality of inter-loop capacitors configured to connect adjacent unit loops respectively, wherein each unit loop comprises a signal channel and further comprises a pair of vertical conducting parts parallel to a cylindrical axis of the coil body, each vertical conducting part comprising an inductor and a first capacitor connected in serial; and a pair of horizontal conducting parts perpendicular to the cylindrical axis of the coil body, at least one horizontal conducting part comprising a second capacitor; and the inter-loop capacitor connects two respective horizontal conducting parts of adjacent unit loops disposed on a same side to eliminate coupling between signal channels of adjacent unit loops.

In accordance with some embodiments, the horizontal conducting part of the unit loop is configured to be an arc-shape.

In accordance with some embodiments, the inductor and first capacitor connected in serial of a vertical conducting part of the unit loop are configured to form a resonant circuit with the inductor and first capacitor connected in serial of an adjacent vertical conducting part of an adjacent unit loop to eliminate coupling between signal channels of the adjacent unit loops.

In accordance with some embodiments, the unit loop is configured to intersect with the adjacent unit loop, and form an overlapped region between adjacent unit loops, and the inductor and first capacitor connected in serial of a vertical conducting part of the unit loop are configured to form a resonant circuit with the inductor and first capacitor connected in serial of an adjacent vertical conducting part of a nonadjacent unit loop separated by one unit loop to eliminate coupling between signal channels of the unit loop and the nonadjacent unit loop separated by one unit loop.

In accordance with some embodiments, the area of the overlapped region between adjacent unit loops is further adjusted to eliminate coupling between signal channels of adjacent unit loops.

In yet another embodiment, a multi-channel nuclear magnetic resonance (NMR) coil operating at a resonance frequency comprises a plurality of unit loops disposed upon a cylindrical surface of a coil body and surrounding the coil body as a closed NMR coil, wherein each unit loop comprises a signal channel and further comprises a pair of vertical conducting parts parallel to a cylindrical axis of the coil body, each vertical conducting part comprising at least a first capacitor; and a pair of horizontal conducting parts perpendicular to the cylindrical axis of the coil body, at least one horizontal conducting part comprising a second capacitor; a plurality of inter-loop capacitors configured to connect adjacent unit loops respectively, the inter-loop capacitor connecting two respective horizontal conducting parts of adjacent unit loops disposed on a same side to eliminate coupling between signal channels of adjacent unit loops; and a plurality of parallel capacitors disposed between adjacent unit loops respectively, each two parallel capacitors forming a resonant circuit with two respective first capacitors of adjacent unit loops to eliminate coupling between signal channels of adjacent unit loops.

In accordance with some embodiments, the multi-channel nuclear magnetic resonance (NMR) coil operating at a resonance frequency further comprises eight unit loops arranged on and surrounding the cylindrical surface, wherein the inter-loop capacitor is configured with a capacitance of 10 pF.

In accordance with some embodiments, the unit loop further comprises a detuning circuit configured to detune the unit loop in a preset time period.

BRIEF DESCRIPTION OF THE DRAWINGS

The aforementioned features and advantages of the invention as well as additional features and advantages thereof will be more clearly understood hereinafter as a result of a detailed description of preferred embodiments when taken in conjunction with the drawings.

Like reference numerals refer to corresponding parts throughout the several views of the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

The invention is further described below with reference to the accompanying drawings and embodiments.

Figure 1:
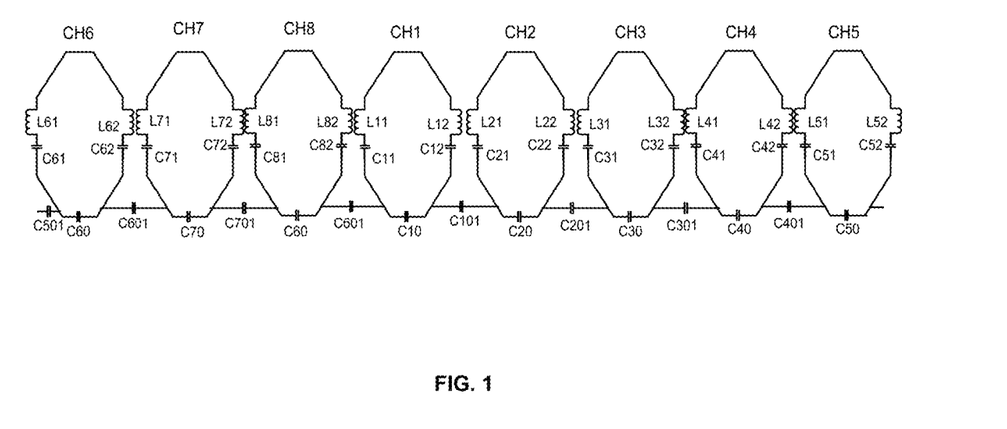
FIG. 1 is a schematic circuit diagram of a multiple channel unit loop NMR coil in an embodiment.

FIG. 1 is a schematic circuit diagram of a multiple channel unit loop NMR coil in an embodiment. FIG. 1 shows an exemplary embodiment having eight channels, and all eight unit loops CH1, CH2, CH3, CH4, CH5, CH6, CH7, and CH8 spread over a planar surface. Each unit loop forms a closed circuit by connecting its one end to the other. When implementing to an NMR imaging device, eight unit loops are disposed on a cylindrical surface of a coil body, and surround the coil body as a closed NMR coil. The inner cavity of the cylindrical coil body is hence the imaging space of the NMR imaging device.

As further shown in FIG. 1, each unit loop comprises a pair of vertical conducting parts parallel to a cylinder axis. For example, in unit loop CH1, a first vertical conducting part comprises an inductor L11 and a capacitor C11 connected in serial, a second vertical conducting part comprises an inductor L12 and a capacitor C12 connected in serial; in unit loop CH2, a first vertical conducting part comprises an inductor L21 and a capacitor C21 connected in serial, a second vertical conducting part comprises an inductor L22 and a capacitor C22 connected in serial; in unit loop CH3, a first vertical conducting part comprises an inductor L31 and a capacitor C31 connected in serial, a second vertical conducting part comprises an inductor L32 and a capacitor C32 connected in serial; in unit loop CH4, a first vertical conducting part comprises an inductor L41 and a capacitor C41 connected in serial, a second vertical conducting part comprises an inductor L42 and a capacitor C42 connected in serial; in unit loop CH5, a first vertical conducting part comprises an inductor L51 and a capacitor C51 connected in serial, a second vertical conducting part comprises an inductor L52 and a capacitor C52 connected in serial; in unit loop CH6, a first vertical conducting part comprises an inductor L61 and a capacitor C61 connected in serial, a second vertical conducting part comprises an inductor L62 and a capacitor C62 connected in serial; in unit loop CH7, a first vertical conducting part comprises an inductor L71 and a capacitor C71 connected in serial, a second vertical conducting part comprises an inductor L72 and a capacitor C72 connected in serial; and in unit loop CH8, a first vertical conducting part comprises an inductor L81 and a capacitor C81 connected in serial, a second vertical conducting part comprises an inductor L82 and a capacitor C82 connected in serial.

In some embodiments, the inductor and capacitor connected in serial of a vertical conducting part of the unit loop are configured to form a resonant circuit with the inductor and capacitor connected in serial of an adjacent vertical conducting part of an adjacent unit loop to eliminate coupling between signal channels of the adjacent unit loops. For example, inductor L12 and capacitor C12 of unit loop CH1 form a resonant circuit with inductor L21 and capacitor C21 of unit loop CH2 at a resonance frequency to eliminate coupling between signal channels of CH1 and CH2.

As shown in FIG. 1, the conducting part along the circumference of the cylindrical coil body and perpendicular to the cylinder axis is called a horizontal conducting part. In some embodiments, the horizontal conducting part is in an arc-shape. Each unit loop comprises a pair of horizontal conducting parts, and at least one horizontal conducting part comprising a capacitor. For example, a horizontal conducting part of unit loop CH1 comprises a capacitor C10; a horizontal conducting part of unit loop CH2 comprises a capacitor C20; a horizontal conducting part of unit loop CH3 comprises a capacitor C30; a horizontal conducting part of unit loop CH4 comprises a capacitor C40; a horizontal conducting part of unit loop CH5 comprises a capacitor C50; a horizontal conducting part of unit loop CH6 comprises a capacitor C60; a horizontal conducting part of unit loop CH7 comprises a capacitor C70; and a horizontal conducting part of unit loop CH8 comprises a capacitor C80.

As further shown in FIG. 1, a plurality of inter-loop capacitors connect two respective horizontal conducting parts of adjacent unit loops disposed on a same side to eliminate coupling between signal channels of adjacent unit loops. For example, inter-loop capacitor C101 connects two respective horizontal conducting parts of CH1 and CH2; inter-loop capacitor C201 connects two respective horizontal conducting parts of CH2 and CH3; inter-loop capacitor C301 connects two respective horizontal conducting parts of CH3 and CH4; inter-loop capacitor C401 connects two respective horizontal conducting parts of CH4 and CH5; inter-loop capacitor C501 connects two respective horizontal conducting parts of CH5 and CH6; inter-loop capacitor C601 connects two respective horizontal conducting parts of CH6 and CH7; and inter-loop capacitor C701 connects two respective horizontal conducting parts of CH7 and CH8. With the plurality of capacitors in the respective horizontal conducting parts, i.e., C10, C20, C30, C40, C50, C60, C70, and C80, and the plurality of inter-loop capacitors, i.e., C101, C201, C301, C401, C501, C601, C701, and C801, the multiple channel NMR coil forms a circle by connecting its one end to the other along one side of the imaging space. The coupling of different unit loops caused by the plurality of capacitors in the respective horizontal conducting parts and the plurality of inter-loop capacitors ensures that each unit loop of the coil can work at the resonance frequency at the same time.

In the above-mentioned embodiment, to decrease the coupling of adjacent channels in the multiple channel NMR coil, mutual inductance decoupling method is exploited for adjacent unit loops. In view of the circuit principle, it is equivalent to inserting a transformer into the coil. The primary and secondary coils of the transformer are respectively connected to the vertical conducting parts of adjacent unit loops. The eddy currents generated by the transformer cancel those generated by coupling. This decoupling method can be applied to adjacent overlap frames, to decrease the electromagnetic coupling of nonadjacent unit loops separated by one unit loop.

In other embodiments of the present invention, both arc-shaped conducting parts of each unit loop in the NMR coil comprise a capacitor each, and a plurality of inter-loop capacitors connect two respective horizontal conducting parts of adjacent unit loops disposed on both same sides such that the unit loops form a closed circle, and to eliminate coupling between signal channels of adjacent unit loops.

Figure 2:
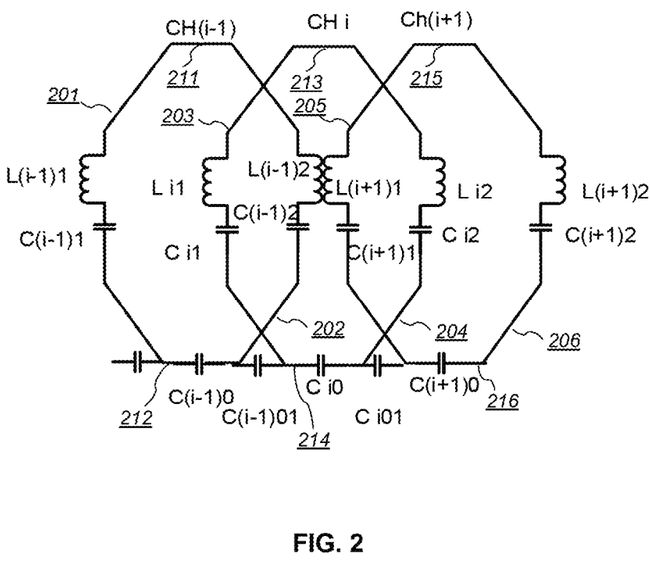
FIG. 2 is a schematic circuit diagram of a multiple channel unit loop NMR coil in another embodiment.

FIG. 2 is a schematic circuit diagram of a multiple channel unit loop NMR coil in another embodiment. FIG. 2 shows three unit loops CH(i−1), CHi, and CH(i+1), where unit loop CH(i−1) comprises a pair of vertical conducting parts 201 and 202, and a pair of horizontal conducting parts 211 and 212; unit loop CHi comprises a pair of vertical conducting parts 203 and 204, and a pair of horizontal conducting parts 213 and 214; and unit loop CH(i+1) comprises a pair of vertical conducting parts 205 and 206, and a pair of horizontal conducting parts 215 and 216. Further, vertical conducting part 201 comprises an inductor L(i−1)1 and a capacitor C(i−1)1; vertical conducting part 202 comprises an inductor L(i−1)2 and a capacitor C(i−1)2; vertical conducting part 203 comprises an inductor Li1 and a capacitor Ci1; vertical conducting part 204 comprises an inductor Li2 and a capacitor Ci2; vertical conducting part 205 comprises an inductor L(i+1)1 and a capacitor C(i+1)1; vertical conducting part 206 comprises an inductor L(i+1)2 and a capacitor C(i+1)2; horizontal conducting part 212 comprises a capacitor C(i−1)0; horizontal conducting part 214 comprises a capacitor Ci0; and horizontal conducting part 216 comprises a capacitor C(i+1)0. Further, inter-loop capacitors C(i−1)01 is configured to connect unit loop CH(i−1) and CHi at the horizontal conducting parts 212 and 214, and inter-loop capacitors Ci01 is configured to connect unit loop CHi and CH(i+1) at the horizontal conducting parts 214 and 216.

In this embodiment, adjacent unit loops cross each other such that each two adjacent unit loops partially overlap. The overlapped region is hence called an overlap area. Additionally, according partial frame (i.e., partial vertical conducting part) of a unit loop is inside its adjacent unit loop, and acts as the overlap area frame, which is hence called an overlap frame. Two vertical conducting parts of each channel unit loop both form two overlap frames, which form overlap areas with two adjacent unit loops, respectively. The size of each overlap area affects the degree of coupling of two adjacent unit loops. By adjusting the size of the overlap area, the coupling of adjacent unit loops can be eliminated. For the vertical conducting parts of two nonadjacent unit loops separated by one unit loop, two vertical conducting parts act as the overlap frames of the two overlap areas in the middle unit loop, and another two vertical conducting parts form adjacent vertical conducting parts, in which inductors and capacitors of the another two vertical conducting parts are used to decrease the coupling of nonadjacent unit loops separated by one unit loop. As shown in FIG. 2, for example, vertical conducting part 203 of CHi and vertical conducting part 202 of CH(i−1) act as the overlap frames of an overlap area; vertical conducting part 204 of CHi and vertical conducting part 205 of CH(i+1) act as the overlap frames of another overlap area; and vertical conducting part 201 of CH(i−1) and vertical conducting part 206 of CH(i+1) become adjacent vertical conducting parts. Further, inductor L(i−1)1 and capacitor C(i−1)1 of vertical conducting part 201 form a resonant circuit with inductor L(i+1)2 and capacitor C(i+1)2 of vertical conducting part 206 to decrease the coupling of nonadjacent unit loops CH(i−1) and CH(i+1) separated by CHi.

Methods for decreasing the coupling of channels in the multiple channel NMR coil are further described below. FIGS. 1 and 2 show schematic diagrams of mutual inductance decoupling method for adjacent unit loops. In view of the circuit principle, it is equivalent to inserting a transformer into the coil. The primary and secondary coils of the transformer are respectively connected to the adjacent overlap frames, or to vertical conductors of adjacent unit loops. The eddy currents generated by the transformer cancel those generated by coupling.

In some embodiments, in the multiple channel unit loop coil, two nonadjacent unit loops separated by one unit loop are decoupled by mutual inductance of overlap frames. As shown in FIG. 2, the overlap frames of unit loops CH(i−1) and CH(i+1) overlapped inside unit loop CHi, i.e., vertical conducting parts 202 and 205 are decoupled by mutual inductance of inductors L(i−1)2, L(i+1)1 and capacitors C(i−1)2, C(i+1)1.

FIG. 2 further demonstrates the spatial decoupling method for adjacent unit loops. The overlap area of two adjacent unit loops leads to electromagnetic induction. According to Faraday's law of induction, the magnetic field generated by the induced current in the two adjacent loops cancels the magnetic field generated by the overlap area of the loops. The integral form of Maxwell-Faraday equation as a generalization of Faraday's law is below:

$$\oint_c E \cdot dl = -\int_s \frac{\partial B}{\partial t} \cdot ds$$

where E is the electric field, B is the magnetic field, C is the contour of the loop, and S is a surface bounded by the loop. Accordingly, while the relative position of two loops is fixed, spatial overlap method can be used to eliminate the strong coupling between adjacent loops.

In some embodiments, in the multiple channel unit loop receive coil, by adjusting the size of the overlap area of adjacent unit loops, the mutual inductance of adjacent unit loops may be zero, thus spatial decoupling is achieved.

Figure 3:
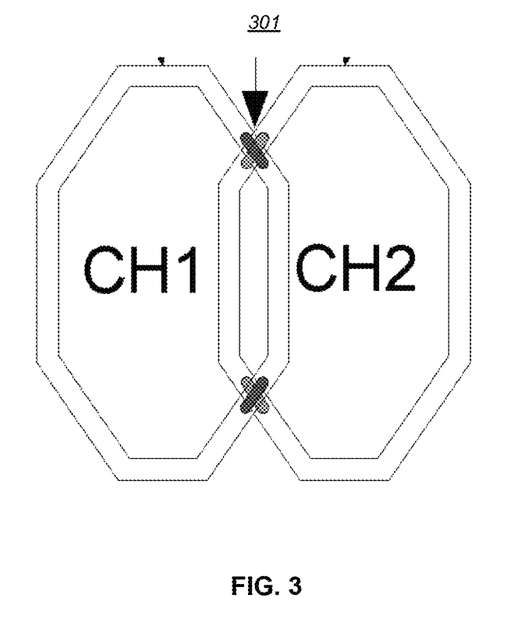
FIG. 3 is a schematic diagram of a decoupling method by decreasing the overlap areas of loop conductors between adjacent loops.

FIG. 3 is a schematic diagram of a decoupling method by decreasing the overlap area of adjacent unit loops. In a typical NMR coil, the vertical and arc-shaped horizontal conducting parts of each unit loop are made of metal foils with certain widths. In view of the knowledge of physics, the capacitance C of a parallel-plate capacitor is proportional to the electric permittivity ϵ, inversely proportional to the plate area S, and inversely proportional to the distance d between two plates. The corresponding equation is shown as below:

$$C = \epsilon s/d$$

where ϵ is the electric permittivity.

In some embodiments as shown in FIG. 3, removing partial area 301 of crossing vertical conducting parts of the overlap frames, or adjusting the distance between crossing vertical conducting parts of the overlap frames decreases the capacitance generated by the overlap of vertical conducting parts and eliminates the coupling of adjacent unit loops.

For example, as shown in FIG. 2, vertical conducting parts 202 and 203 of the overlap frames of adjacent unit loops CH(i−1) and CHi overlap. The overlap of vertical conducting parts 202 and 203 generates capacitance. The capacitance can be decreased by adjusting the distance between those vertical conducting parts 202 and 203 or by adjusting the size of the overlap area of those vertical conducting parts 202 and 203.

Figure 4:
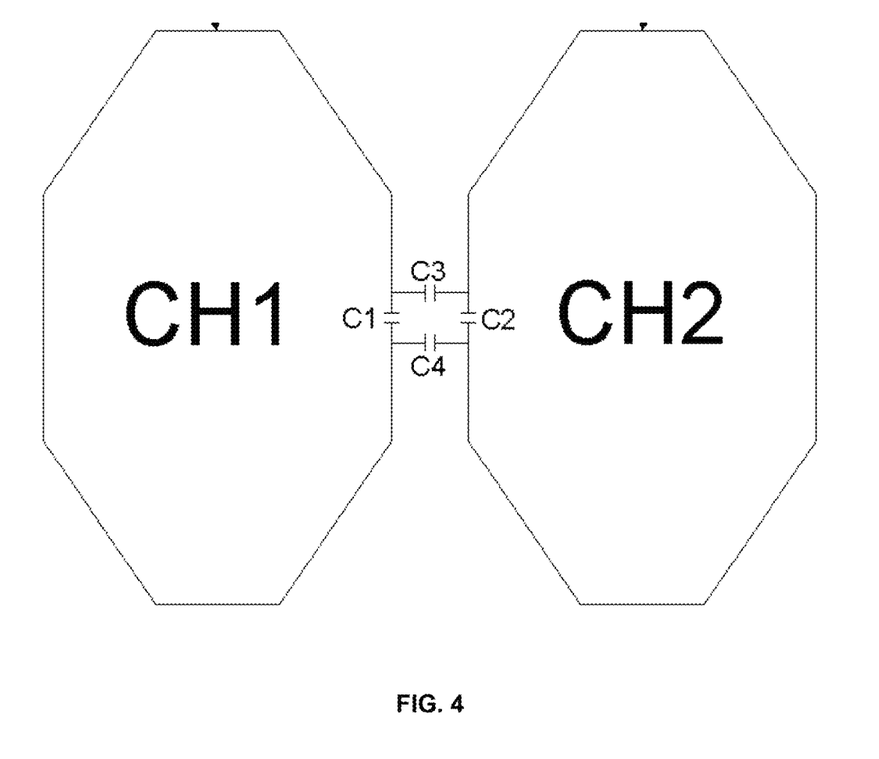
FIG. 4 is a schematic diagram of decoupling method by parallel resonant capacitors between adjacent loops.

FIG. 4 is a schematic diagram of a decoupling method by parallel resonant capacitors. A pair of capacitors C3 and C4 with suitable capacitance are arranged between two adjacent unit loops CH1 and CH2, and connect the capacitor C1 of unit loop CH1 and the capacitor C2 of unit loop C2 in parallel, such that when the resonance occurs, the capacitor and the inductance between adjacent unit loops exhibit a parallel resonance. The resistance is so large that the induced current is quite small, leading to decoupling of adjacent unit loops. Comparing to FIG. 2 where mutual inductance decoupling is implemented, inductors can achieve the same decoupling as capacitors, but decoupling by inductors causes more loss than decoupling by capacitors. Furthermore, capacitors can transmit RF signals.

In some embodiments, adjacent unit loops can further connect with each other by a plurality of inter-loop capacitors between unit loops. For example, inter-loop capacitor C(i−1)01 is configured to connect unit loop CH(i−1) and CHi at the horizontal conducting parts 212 and 214, and inter-loop capacitor Ci01 is configured to connect unit loop Chi and CH(i+1) at the horizontal conducting parts 214 and 216, as shown in FIG. 2. Moreover, at least one arc-shaped horizontal conducting part of a unit loop includes a capacitor, for example, horizontal conducting part 212 comprises a capacitor C(i−1)0; horizontal conducting part 214 comprises a capacitor Ci0; and horizontal conducting part 216 comprises a capacitor C(i+1)0. Such a continuous loop by end to end connection of series capacitors decreases the overall coupling of the coil and improves the coil quality.

Figure 5:
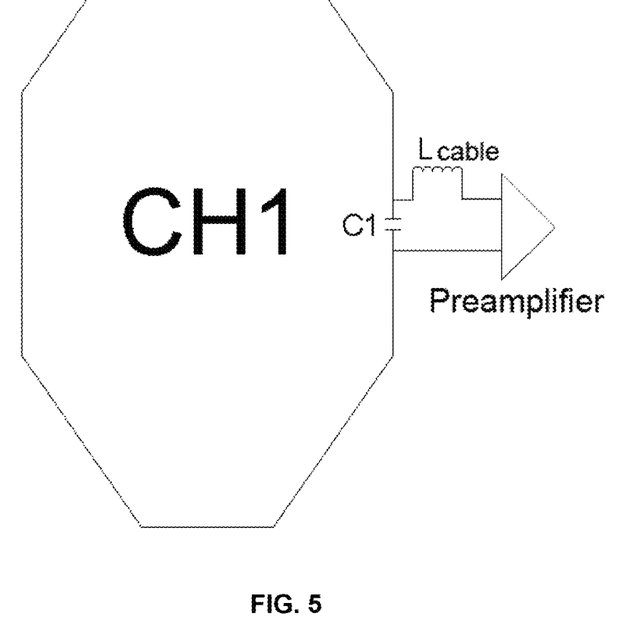
FIG. 5 is a schematic diagram of decoupling method by connection of a preamplifier.

FIG. 5 is a schematic diagram of a decoupling method by connection of a preamplifier. In a resonance state, a preamplifier can be equivalent to a resistance, and the L cable connected to the coil brings up distributed inductance. The preamplifier, capacitor C1 and the L cable exhibit a parallel resonance at the resonance frequency. The resistance is so large that the induced current is quite small, leading to decoupling of adjacent unit loops. This decoupling method can also be used to eliminate the weak coupling of nonadjacent unit loops in the coil.

Further, the tuning method of the receive coil is illustrated below and explained with an example of an eight channel (8CH) unit loop knee receive coil.

Figure 6:
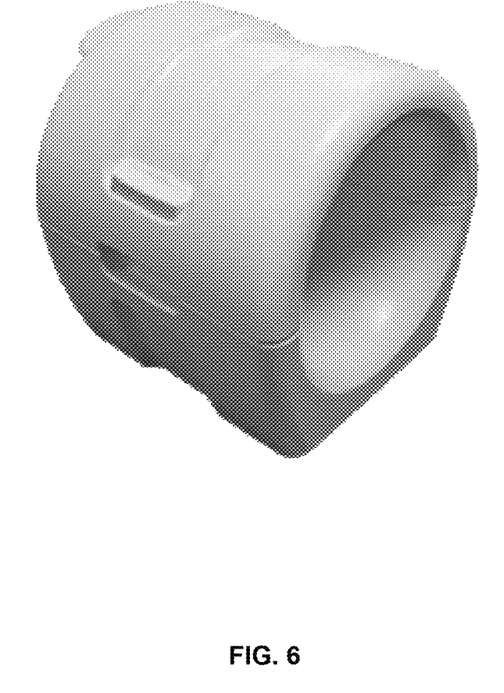
FIG. 6 is an overall exterior picture of an NMR imaging system having a multiple channel unit loop NMR coil in an embodiment.

FIG. 6 is an overall exterior picture of an NMR imaging system having an 8CH knee receive loop in the present invention.

Figure 7:
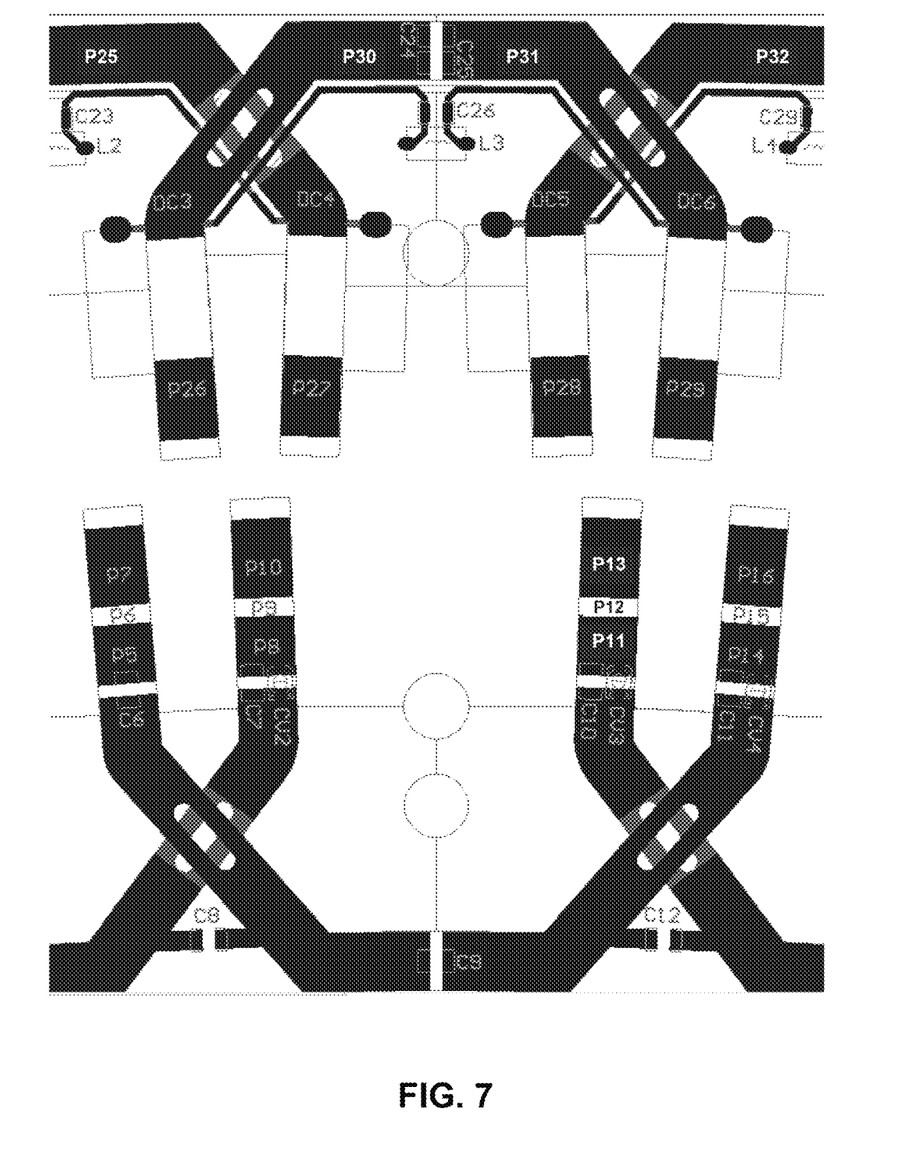
FIG. 7 is the printed circuit board (PCB) wiring diagram of a unit loop in an embodiment.

FIG. 7 is the PCB wiring diagram of a unit loop in an embodiment. In this embodiment, the unit loop comprising a plurality of electrodes P5-P7, P14-P16, P26, P29, P30, and P31, capacitors C6, C9, C11, C24-C26, detuning circuits DC3 and DC6, and an inductor L3 corresponds to unit loop CHI of FIG. 1. The unit loop comprising P32, DC5, P28, P11-P13, C10, and CV3 corresponds to unit loop CH2 of FIG. 1. The unit loop comprising P25, DC4, P27, P8-P 10, C7, and CV2 corresponds to unit loop CH8 of FIG. 1. Capacitor C8 is an inter-loop capacitor connecting unit loop CH1 and CH8; and capacitor C12 is another inter-loop capacitor connecting unit loop CHI and CH2.

The configuration of unit loop CH1 is detailed as below:

Decoupling inductors are welded between P6 and P5 as well as between P15 and P14, and form mutual inductance with decoupling inductors in corresponding overlap frames of unit loops CH7 and CH3 (i.e., non-adjacent unit loops to CH1 separated by one unit loop as shown in FIG. 1), respectively. P26 is electrically connected with P7, which constitutes the first overlap frame of unit loop CH1. P29 is electrically connected with P16, which constitutes the second overlap frame of unit loop CH1. Capacitors C24 and C25 are welded between P30 and P31 in parallel.

In the working periods of RF transmission in the NMR system, detuning circuits DC3 and DC6 are loaded such that the receive coil is disconnected in the detuned state; in the working periods of RF receiving in the NMR system, detuning circuits DC3 and DC6 are connected such that the receive coil is in the resonance working state. The decoupling method is shown in FIG. 2. The detuning circuits DC3 and DC6 are connected to a DC power supply. Capacitor C26 and inductor L3 are connected in parallel between the detuning circuits DC3 and DC6. When the detuning circuits DC3 and DC6 are loaded, a magnetic resonance signal flows through the inductor L3. The capacitor C26 and inductor L3 work at the resonance frequency to increase the impedance such that the flow of the magnetic resonance signal can be effectively blocked, and the receive coil is disconnected in the detuned state.

In some embodiments, for tuning purpose, adjustable capacitor CV4 is employed in one vertical conducting part of CH1 and connected to C11 in parallel to equalize the electric current flowing through CH1. Further, adjustable capacitors C24 and C25 connected in parallel are employed in one horizontal conducting part of CH1 in order to meet the requirement of the capacitance accuracy.

In some embodiments, P27 is electrically connected with P10, which constitutes the second overlap frame of unit loop CH8 (i.e., adjacent unit loop to CH1 as shown in FIG. 1). By adjusting the relative position of the first overlap frame of unit loop CH1 and the second overlap frame of unit loop CH8, the overlap area of unit loops CHI and CH8 is adjusted. Similarly, P28 is electrically connected with P13, which constitutes the first overlap frame of unit loop CH2 (i.e., adjacent unit loop to CHI as shown in FIG. 1). By adjusting the relative position of the second overlap frame of unit loop CH1 and the first overlap frame of unit loop CH2, the overlap area of unit loops CH1 and CH2 is adjusted. By adjusting the size of the overlap area of adjacent unit loops, the coupling of adjacent unit loops can be changed. The decoupling method is shown in FIG. 3.

Further, decoupling inductors are welded between P8 and P9 as well as between P11 and P12, and form an eddy current so as to eliminate the coupling between CH2 and CH8.

In some embodiment, capacitors C8 and C12 are configured to change the coupling of unit loop CH1 with unit loops CH4, CH5 and CH6 in the receive coil.

As an 8CH unit loop knee receive coil, as shown in FIG. 7, it has a capacitance distribution as follows: C24 is 200 pF, C6 is 130 pF, C11 is 110 pF, CV4 is 24 pF (adjustable), C9 is 200 pF, C8 and C12 are both 10 pF. By adjusting the capacitance of adjustable capacitors C24, C25 and CV4, the magnetic resonance imaging (MRI) RF coil matches a 50.Ω. preamplifier.

The tuning method of an 8CH unit loop knee receive coil, as an embodiment of the present invention, is explained below and depicted with an example of unit loop CH1.

First, disconnect capacitors C8 and C12 in the way shown in FIG. 2. Adjust the relative positions of P26-P7 and P27-P10, and meanwhile measure the degree of coupling between unit loops CH1 and CH8 with a network analyzer, until the signal attenuation of mutual coupling is less than −15 dB. Similarly, adjust the relative positions of P29-P16 and P28-P13 to change the overlap area of unit loops CH1 and CH2, and measure the degree of coupling with a network analyzer, until the coupling signal reduces to less than −15 dB.

Second, adjust the decoupling inductors welded between P6 and P5 as well as between P15 and P14, such that the coupling reduces to less than 20 dB between unit loops CH1 and CH3 as well as between unit loops CH1 and CH7.

Meanwhile, measure the coupling signal attenuations between unit loops CH1 and CH4, between unit loops CH1 and CH5, as well as between unit loops CH1 and CH6. All of them are greater than −6 dB, which is too high to be eliminated by low impedance preamplifiers. The decoupling method in some embodiments of the present invention therefore increases the capacitance of capacitors C8 and C12 by increasing the capacitance stepwise from 5 pF. The presence of capacitors C8 and C12 transmits partial signals to adjacent unit loops, which is equivalent to increase the coupling of adjacent unit loops. As the capacitance of capacitors C8 and C12 increases, monitor and measure with a network analyzer the signal coupling between unit loops CH1 and CH4, between unit loops CH1 and CH5, as well as between unit loops CH1 and CH6, until the coupling signals reduce to −10 dB, which can be eliminated by a signal output circuit made of low impedance preamplifiers. In some embodiments, the capacitance of capacitors C8 and C12 is 10 pF.

Third, decoupling method by decreasing the overlap areas of the vertical conducting parts of unit loops, as shown in FIG. 3, is exploited. Remove a partial area of crossing vertical conducting parts of the overlap frames, adjust the distance between the overlapped vertical conducting parts of the overlap frames, and monitor and measure with a network analyzer the coupling between unit loops CH1 and CH2 as well as between unit loops CH1 and CH8. In the present embodiment, the distance between the overlapped vertical conducting parts of the overlap frames is preferred to be an interval of 3 mm, optimal to eliminate the coupling of adjacent unit loops. As a result, the coupling of channel units in the 8CH knee coil is eliminated.

Finally, the tuning method is repeated with each unit loop of the 8CH unit loop NMR receive coil, such that a multiple channel NMR receive coil with a high SNR is achieved.

The above-mentioned embodiments are preferred ones of the present invention, which is not limited to those embodiments. Equivalent or simple modifications made according to the ideas of the present invention and the described constructions, features, and principles all fall within the protection scope of the present invention.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

I claim:

1. A multiple channel nuclear magnetic resonance (NMR) coil, operating at a resonance frequency $f_0$, comprising:
    five or more closed signal channels, each comprising a unit loop, the unit loops being arranged on and surrounding a cylindrical surface of a periphery of an imaged region, and each unit loop comprises:
    two vertical conducting parts parallel to a cylinder axis; and
    two arc-shaped conducting parts perpendicular to the cylinder axis;
    wherein the vertical conducting part of the unit loop comprise an inductor and a capacitor connected in serial, forming a resonant circuit with another inductor and capacitor in an adjacent unit loop or a nonadjacent unit loop separated by one unit loop to decrease coupling between signal channels of adjacent unit loops or nonadjacent unit loops separated by one unit loop; and
    a plurality of inter-loop capacitors configured to respectively connect the two arc-shaped conducting parts disposed on one same side of adjacent unit loops to decrease coupling between multiple signal channels.

2. The multiple channel nuclear magnetic resonance (NMR) coil according to claim 1, wherein
    at least one arc-shaped conducting part of each unit loop further comprises an intra-loop capacitor to decrease the coupling between multiple signal channels.

3. The multiple channel nuclear magnetic resonance (NMR) coil according to claim 1, wherein
    both arc-shaped conducting parts of each unit loop comprise an intra-loop capacitor, respectively, and
    the plurality of inter-loop capacitors are further configured to respectively connect the arc-shaped conducting parts disposed on both same sides of adjacent unit loops.

4. The multiple channel nuclear magnetic resonance (NMR) coil according to claim 1, wherein
    each unit loop overlaps with an adjacent unit loop to form an overlapped area that generates a mutual inductance, forming the resonant circuit by coupling the mutual inductance with two respective capacitors of adjacent unit loops to decrease the coupling of adjacent signal channels.

5. The multiple channel nuclear magnetic resonance (NMR) coil according to claim 4, wherein
    the unit loops are further configured to change a size of the overlapped area to decrease the coupling of adjacent signal channels.

6. The multiple channel nuclear magnetic resonance (NMR) coil according to claim 4, wherein
    a size of the overlap area is configured such that the coupling of adjacent unit loops is less than −15 dB.

7. The multiple channel nuclear magnetic resonance (NMR) coil according to claim 4, wherein
    a vertical height of the overlapped area is configured to be 3 mm.

8. The multiple channel nuclear magnetic resonance (NMR) coil according to claim 1, wherein
    two respective inductors of adjacent unit loops or nonadjacent unit loops separated by one unit loop generates an eddy current that offsets a coupling eddy current to decrease the coupling between adjacent signal channels or nonadjacent signal channels separated by one signal channel.

9. The multiple channel nuclear magnetic resonance (NMR) coil according to claim 1, further comprises eight unit loops arranged on and surrounding the cylindrical surface, wherein the inter-loop capacitor is configured with a capacitance of 10 pF.

10. The multiple channel nuclear magnetic resonance (NMR) coil according to claim 1, wherein the unit loop further comprises a detuning circuit configured to detune the unit loop in a preset time period.

11. A multi-channel nuclear magnetic resonance (NMR) coil operating at a resonance frequency comprising:
    a plurality of unit loops disposed upon a cylindrical surface of a coil body and surrounding the coil body as a closed NMR coil; and
    a plurality of inter-loop capacitors configured to connect adjacent unit loops respectively, wherein
    each unit loop comprises a signal channel and further comprises:

a pair of vertical conducting parts parallel to a cylindrical axis of the coil body, each vertical conducting part comprising an inductor and a first capacitor connected in serial; and a pair of horizontal conducting parts perpendicular to the cylindrical axis of the coil body, at least one horizontal conducting part comprising a second capacitor;

and the inter-loop capacitor connects two respective horizontal conducting parts of adjacent unit loops disposed on a same side to eliminate coupling between signal channels of adjacent unit loops.

12. The multi-channel nuclear magnetic resonance (NMR) coil operating at a resonance frequency according to claim 11, wherein the horizontal conducting part of the unit loop is configured to be an arc-shape.

13. The multi-channel nuclear magnetic resonance (NMR) coil operating at a resonance frequency according to claim 11, wherein the inductor and first capacitor connected in serial of a vertical conducting part of the unit loop are configured to form a resonant circuit with the inductor and first capacitor connected in serial of an adjacent vertical conducting part of an adjacent unit loop to eliminate coupling between signal channels of the adjacent unit loops.

14. The multi-channel nuclear magnetic resonance (NMR) coil operating at a resonance frequency according to claim 11, wherein the unit loop is configured to intersect with the adjacent unit loop, and form an overlapped region between adjacent unit loops, and the inductor and first capacitor connected in serial of a vertical conducting part of the unit loop are configured to form a resonant circuit with the inductor and first capacitor connected in serial of an adjacent vertical conducting part of a nonadjacent unit loop separated by one unit loop to eliminate coupling between signal channels of the unit loop and the nonadjacent unit loop separated by one unit loop.

15. The multi-channel nuclear magnetic resonance (NMR) coil operating at a resonance frequency according to claim 14, wherein the area of the overlapped region between adjacent unit loops is further adjusted to eliminate coupling between signal channels of adjacent unit loops.

16. A multi-channel nuclear magnetic resonance (NMR) coil operating at a resonance frequency comprising:

a plurality of unit loops disposed upon a cylindrical surface of a coil body and surrounding the coil body as a closed NMR coil, wherein each unit loop comprises a signal channel and further comprises:

a pair of vertical conducting parts parallel to a cylindrical axis of the coil body, each vertical conducting part comprising at least a first capacitor; and a pair of horizontal conducting parts perpendicular to the cylindrical axis of the coil body, at least one horizontal conducting part comprising a second capacitor;

a plurality of inter-loop capacitors configured to connect adjacent unit loops respectively, the inter-loop capacitor connecting two respective horizontal conducting parts of adjacent unit loops disposed on a same side to eliminate coupling between signal channels of adjacent unit loops; and a plurality of parallel capacitors disposed between adjacent unit loops respectively, each two parallel capacitors forming a resonant circuit with two respective first capacitors of adjacent unit loops to eliminate coupling between signal channels of adjacent unit loops.

17. The multi-channel nuclear magnetic resonance (NMR) coil operating at a resonance frequency according to claim 16, further comprises eight unit loops arranged on and surrounding the cylindrical surface, wherein the inter-loop capacitor is configured with a capacitance of 10 pF.

18. The multiple channel nuclear magnetic resonance (NMR) coil according to claim 16, wherein the unit loop further comprises a detuning circuit configured to detune the unit loop in a preset time period.

* * * * *